United States Patent
Hennings et al.

(10) Patent No.: US 7,247,782 B2
(45) Date of Patent: Jul. 24, 2007

(54) GENETIC MUSIC

(76) Inventors: Mark R. Hennings, 8600 NE. Delaney Rd., Kingston, WA (US) 98346; Denise M. Kettelberger, 1775 Humboldt Ave. South, Minneapolis, MN (US) 55403

( * ) Notice: Subject to any disclaimer, the term of this patent is extended or adjusted under 35 U.S.C. 154(b) by 44 days.

(21) Appl. No.: 10/754,914

(22) Filed: Jan. 8, 2004

(65) Prior Publication Data

US 2004/0255757 A1    Dec. 23, 2004

Related U.S. Application Data

(60) Provisional application No. 60/441,984, filed on Jan. 22, 2003, provisional application No. 60/439,061, filed on Jan. 8, 2003.

(51) Int. Cl.
*G10H 1/00*    (2006.01)
(52) U.S. Cl. .......................... 84/600; 84/616
(58) Field of Classification Search ........... 84/600–609
See application file for complete search history.

(56) References Cited

U.S. PATENT DOCUMENTS

| | | | |
|---|---|---|---|
| 5,856,928 A | 1/1999 | Yan | |
| 6,125,331 A | 9/2000 | Toh | |
| 6,172,941 B1 | 1/2001 | Bieramperl | |
| 6,266,654 B1 | 7/2001 | Schull | |
| 7,064,262 B2 * | 6/2006 | Klefenz et al. | ................ 84/616 |
| 2004/0060424 A1 * | 4/2004 | Klefenz et al. | ................ 84/616 |
| 2005/0115381 A1 * | 6/2005 | Bryden et al. | ................ 84/600 |

FOREIGN PATENT DOCUMENTS

GB    2350469 A  *  5/1989
GB    2350469 A  *  11/2000

OTHER PUBLICATIONS

Inflections: Music from DNA. Dunn, J. and K. W. Bridges. 1992-1995. Viewed online on Jul. 11, 2005 at www.botany.hawaii.edu/faculty/bridges/inflections/mp3.*
Welsh Software turns DNA into music. May 14, 2001. News Wales. Viewed online on Jul. 11, 2005 at □□www.newswales.co.uk/?F=1&section=Culture&id=3932.*
Gene Sequence Analyis with Auditory Display. Munakata, N. Viewed online on Jul. 11, 2005—data of publication unknown. □□www.toshima.ne.jp/~edogiku/GSAwAD.html.*
www.whozoo.org/mac/music viewed online Mar. 2, 2007.*
www.algoart.com viewed online Mar. 2, 2007.*
http://amas.cz3.nus.edu.sg/music/ viewed online Mar. 2, 2007.*
www.genomamusic.com/genoma/ing/inicio viewed online Mar. 2, 2007.*

(Continued)

*Primary Examiner*—Lincoln Donovan
*Assistant Examiner*—David S. Warren

(57) ABSTRACT

Genetic music generated by decoding and transcribing genetic information within a DNA sequence into a music signal having melody and harmony, and useful in the producion of novely consumer products, identification systems, and diagnostic tools.

23 Claims, 4 Drawing Sheets

OTHER PUBLICATIONS de la Cruz, 1995-2003, *The Nucleic Acid Database Project*, Rutgers, The State of New Jersey, http://ndbserver.rutgers.edu/atlas/music/proj.1.html, pp. 1-4 "Project 1 (Plain Melody & Compositioñ 1)."

Gena et al., 2001, http://www.artic.edu/~pgena/docs/gena-strom-DNA.pdf, pp. 1-7 "A Physiological Approach to DNA Music."

Gena et al., *Sixth International Syumposium on Electronic Art*, Montreal, 1995: 83-85. *XI Colloquio di Informatica Musicale*, Univeristà di Bologna, 1995: 203-204. http://www.artic.edu/~pgena/docs/CIMXI-gena-strom.pdf, pp. 1-2 "Musical Synthesis of DNA Sequences."

\* cited by examiner

GENETIC MUSIC

BACKGROUND OF THE INVENTION

Genetic material identifies the characteristics that are common to living organisims, as well as unique characteristics of every individual plant and animal. The recent acceleration in our knowledge of specific sequences as well as total genomes has also provided tools for rapidly obtaining this information from a small sample of biological material. Numerous products and methods can now take advantage of this pool of knowledge, adapting the genetic material into novel and interesting new products.

Genetic material includes nucleic acid sequences, DNA and RNA, that are arrangements of four different nucleotides, Adenine (A), cytosine (C), thymine (T), and guanine (G) are the building blocks of a DNA sequence. Much of the DNA in an individual genome encodes the amino acids of specific proteins using a triplet codon of nucleotides to code for each specific amino acid, as well as to signal the start and stop of the encoded protein. Non-coding DNA includes regulatory sequences and signals for the processing of the coded messages. The data stored in an individual's genome can be determined by various known sequencing methods, and this data can then be tapped for a variety of purposes, including individual identification, medical diagnosis, and the like.

SUMMARY OF THE INVENTION

The present invention takes advantage of the advances in genetic sequence knowledge and provides a creative solution to analysis of sequence data. In the present invention, genetic sequence data is converted into music characteristic of the individual sequence provided. This genetic music is useful in a variety of products, including medical diagnostics, security identification systems, novelty items such as greeting cards, and the like.

DETAILED DESCRIPTION OF THE INVENTION

Figure 1:
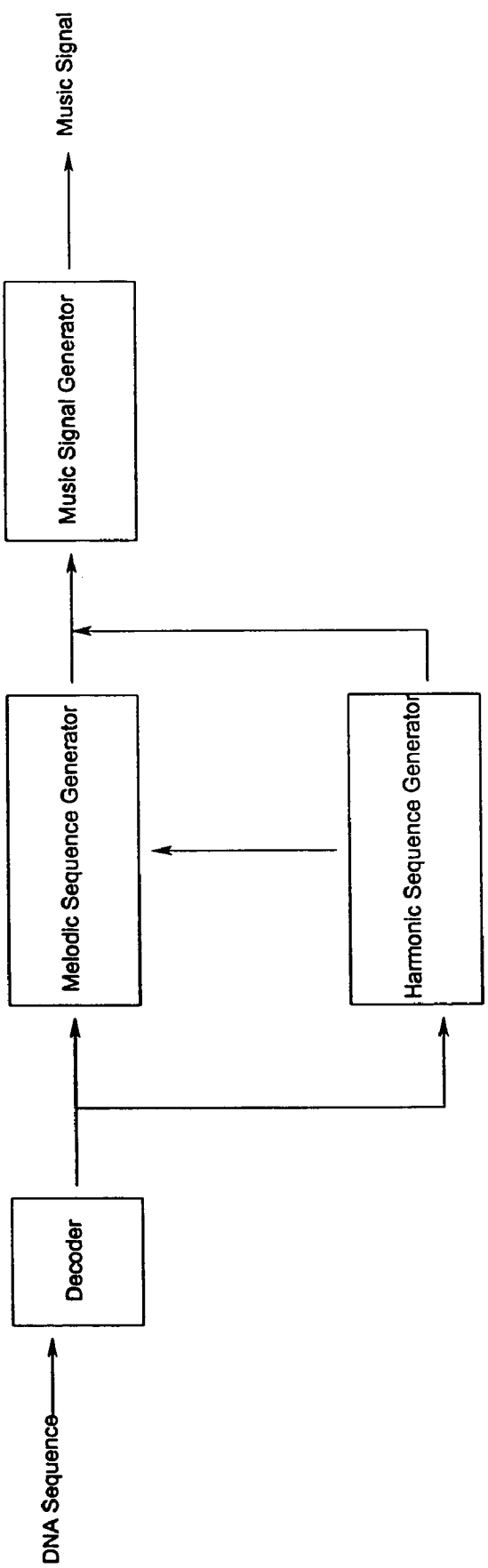
FIG. 1 is a schematic diagram demonstrating the generation of a music signal from a DNA sequence sample according to one embodiment of the invention.

Definitions:

As used herein, the following terms are intended to have the noted definitions.

"melodic sequence" is a signal containing melodic information.

"harmonic sequence" is a signal containing musical harmonic information.

"chord" is musical information comprising notes of typically three or more intervals.

"transcriber" is an apparatus configured to receive one data signal and transcribe that data signal into a different data signal; in the present invention, the received DNA signal is transcribed into a musical signal.

"generator" is an apparatus configured to generate a data signal; in the present invention, a musical signal is generated.

"decoder" is an apparatus configured to decode a message within a data signal; in the present invention, the received DNA signal is decoded to determine an amino acid signal.

"music signal" is the music product generated from the data stream; in the present invention, the music signal is generated from received DNA sequence that is decoded and may be melodic music, harmonic music, or a combination of these.

"audio waveform" is a digital or analog signal conveying an audio "recording" of the intended music.

"musical command sequence" is a sequence of commands for a generator (such as a synthesizer) to generate music according to the command sequence.

"data carrier" is an apparatus configured and adapted to carry a data signal; in the present invention, a data carrier may be an electronic medium such as a computer, a compact disk (CD), and the like.

"consumer product" is a product purchased and/or used by consumers.

"clinical analyzer" is an apparatus configured to analyze data from patient samples.

Genetic Material

Genetic material is contained within cells in genomic DNA. The nucleotide bases of genomic DNA (A, C, T, and G) encode the twenty amino acids that are the builiding blocks of proteins, as well as signals for start and stop of the three base codon translation into amino acids. In the cell, the code within the genomic DNA is copied to messenger RNA, where the nucleotide thymine (T) is replaced with uracil (U). In artifical systems, the messenger RNA can be obtained from cells and converted into DNA as a copy of the RNA message, called cDNA. Genomic DNA contains additional signals that are not part of the coding sequence.

The codon table below shows the code for translation of DNA triplets into amino acids.

| | | CODON TABLE | | | |
|---|---|---|---|---|---|
| First | T/U | C | A | G | Last |
| T/U | Phe | Ser | Tyr | Cys | T/U |
| | Phe | Ser | Tyr | Cys | C |
| | Leu | Ser | Stop (Ochre) | Stop (Umber) | A |
| | Leu | Ser | Stop (Amber) | Trp | G |
| C | Leu | Pro | His | Arg | T/U |
| | Leu | Pro | His | Arg | C |
| | Leu | Pro | Gln | Arg | A |
| | Leu | Pro | Gln | Arg | G |
| A | Ile | Thr | Asn | Ser | T/U |
| | Ile | Thr | Asn | Ser | C |
| | Ile | Thr | Lys | Arg | A |
| | Met | Thr | Lys | Arg | G |
| G | Val | Ala | Asp | Gly | T/U |
| | Val | Ala | Asp | Gly | C |
| | Val | Ala | Glu | Gly | A |
| | Val | Ala | Glu | Gly | G |

Sequencing

DNA can be sequenced from a variety of cell samples, including blood, hair, nail clippings, cheek cells, and the like. Known methods include didioxy sequencing, PCR sequencing, and the like. Random pieces of DNA extracted from cells may be sequenced, or specific portions may be isolated and sequenced, for example by targeted PCR amplification of a particular region of the DNA. Once the sample has been sequenced, it can be stored, for example, in an electronic data carrier, for transmission to a DNA transcriber for use in generating music according to the present invention.

Music

A musical composition is a collection of music notes that can include a melody, harmony, tempo, rhythm, volume, and the like. Depending upon the algorithm applied to a data stream, synthetic music can be generated in a variety of ways from simple to complex. In the simplest method, each of the DNA nucleotides A, C, T, and G can be assigned a specific musical note. The data stream of nucleotides can then be transcribed into a data stream of musical notes. Alternatively, the nucleotide sequence can first be decoded to an amino acid sequence, whereby the twenty amino acids can be each assigned to a specific musical note. Variations can be used to produce chords, to specify rhythms, tone, volume, to generate melodic music and harmonic music, and the like.

As shown in FIG. 1, according to the present invention, a data stream of nucleotides of a DNA sequence is provided to a decoder. The decoder detects specific nucleotide sequences that may be recognition signals, enzyme recognition signals, promoter sequences, and the like. The decoder may also detect a coding sequence, for example a sequence having an open reading frame with start and stop signals, and intervening codon sequences. The DNA sequence received by the decoder is processed according to one set of recognition sequences and transcribed by a melodic sequence generator into a melodic sequence in response to the received DNA sequence. The decoder further processes the received DNA sequence into an amino acid sequence according to the identified triplet codon series, and conveys information related to the determined amino acids in a signal. In one embodiment, the harmonic sequence generator determines a series of chords according to the determined amino acid. The harmonic information can be used by the melodic sequence generator to develop a melodic sequence. Further, the harmonic sequence generator can identify chemical proerties that are associated with the determined amino acids. The melody and harmony generated are then processed into a music signal by a music signal generator.

Figure 2:
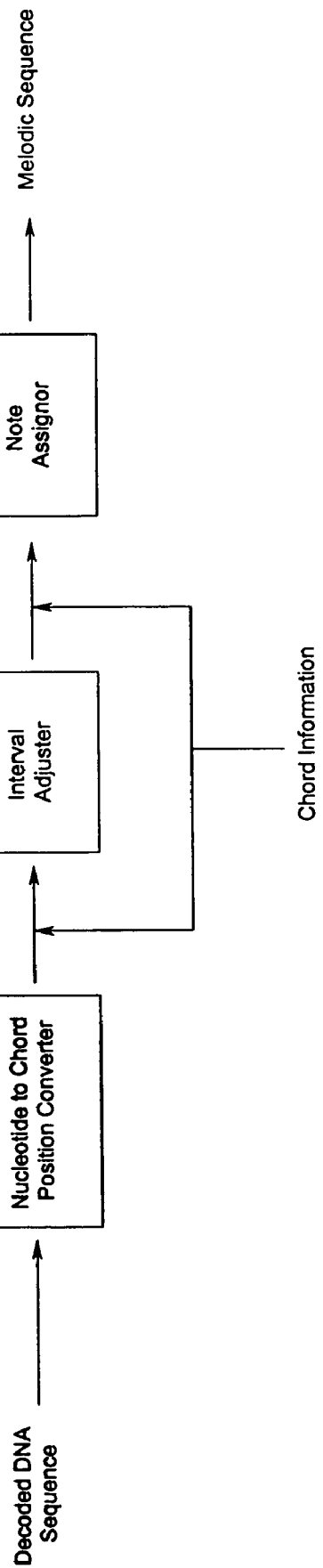
FIG. 2 is a schematic diagram demonstrating the generation of a music signal from a DNA sequence sample according to one embodiment of the invention.

As shown in FIG. 2, in one embodiment, a melodic sequence is produced from the decoded DNA sequence by assigning each nucleotide to a chord position converter. The chord information is adjusted by an internal adjuster to produce a series of notes to generate a melodic sequence. The adjuster may use harmonic sequence information to assign notes in the melody as chord tones or passing tones.

Figure 3:
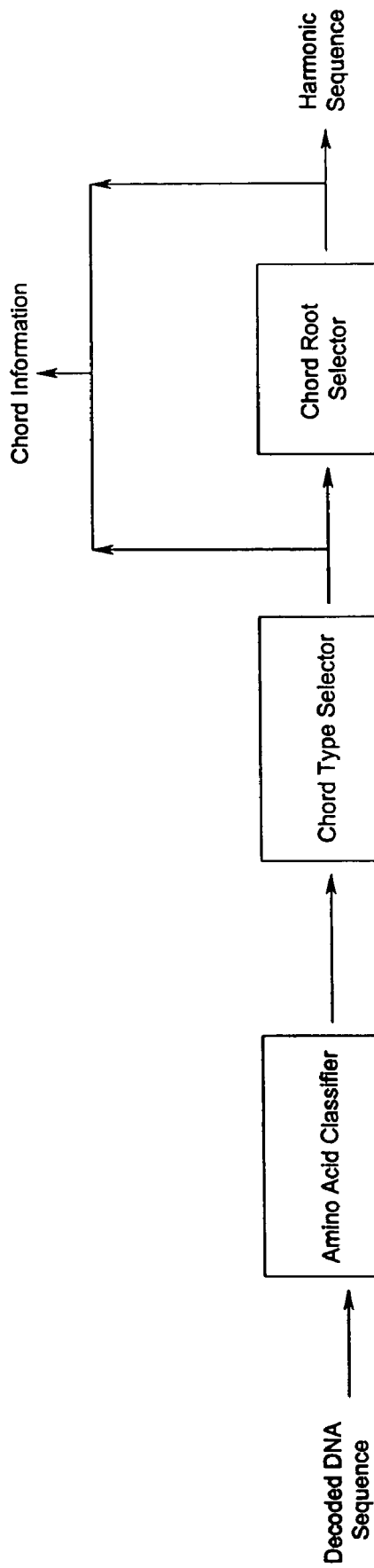
FIG. 3 is a schematic diagram demonstrating the generation of a music signal from a DNA sequence sample according to one embodiment of the invention.

As shown in FIG. 3, in one embodiment, a harmonic sequence is produced from the decoded DNA sequence by classifying each amino acid identified from the DNA sequence. The classification can be according to a chemical property (such as "hydrophobic" or acidity) and/or simply by the amino acid name. The classification data is converted into chord types by a chord type selector that selects chord roots to produce a harmonic sequence. At the same time, the chord type and root selectors provide chord information that can be applied to the adjustment of data to obtain the melodic sequence, as shown in FIG. 2.

Figure 4:
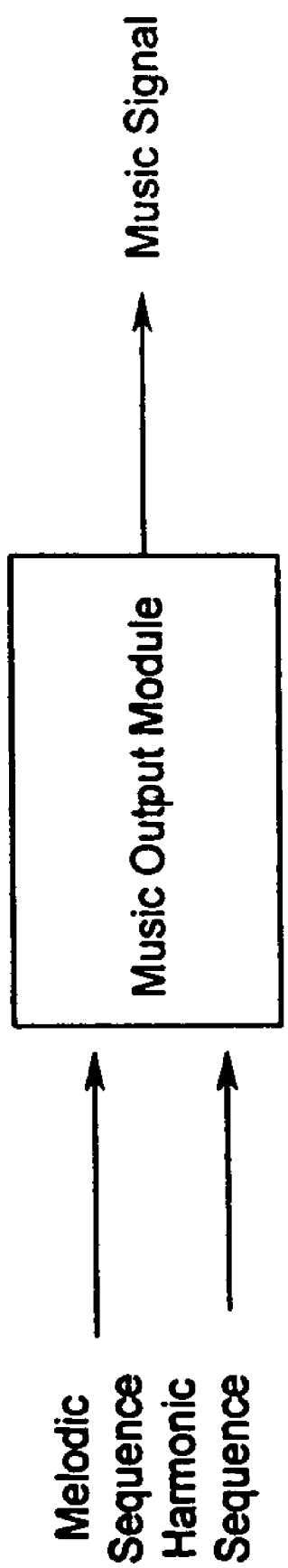
FIG. 4 is a schematic diagram demonstrating the generation of a music signal from a DNA sequence sample according to one embodiment of the invention.

As shown in FIG. 4, the melodic sequence and the harmonic sequence are received by a music output module to produce the product music signal. The music signal may be an audio waveform that can be played on commercial music players or music command sequences (such as MIDI files or data streams) that can be used to control devices that generate music (such as musical synthesizers).

Products

The music signal generated from the genetic data can be used in a variety of consumer and industrial products and methods. For example, novelty products such as greeting cards, genetic music CDs, and the like can incorporate a person's individual music generated from their own sample of DNA. The specific DNA sequence can be provided to a company for generation of the genetic music. Alternatively, a sample containing the genetic material can be provided for sequencing and generating the music.

Useful products include individual identity analysis, for example, for security checking, paternity testing, and the like. The music generated by an individual sample can be compared with a control sample. An identity analyzer can be configured to provide an audible signal for a specific comparative result, for example, if the sample and the control differ, e.g., signaling an alarm in a security setting, or when they are the same, e.g., adding excitement to live television coverage of paternity determinations.

Clinical analyzers that compare sequences of patient samples with controls may be programmed to provide soothing melodies when the sequence is "normal" and to provide an audible, for example, discordant music when an "abnormal" sequence is detected. Such signals can provide a signal for the clinical technician to alert a physician to the difference in the sequence.

The above specification, examples, figures, and data provide a complete description of the invention. Since many embodiments of the invention can be made without departing from the spirit and scope of the invention, the invention resides in the claims hereinafter appended.

We claim:

1. An apparatus for generating music, comprising:
   a. a harmonic sequence generator that is configured to receive a nucleotide sequence, determine an amino acid that is defined by a three-segment nucleotide sequence, and determine a chord in response to the defined amino acid, whereby a harmonic sequence is generated in response to a succession of defined amino acids; and
   b. a melodic sequence generator that is configured to receive the nucleotide sequence and the chords generated from the determined amino acid sequence, and generate a melodic sequence of tones in response to the received nucleotide sequence within the determined chords.

2. The apparatus of claim 1, further comprising a decoder that is configured to determine codons within the DNA sequence and synchronize the harmonic sequence generator in response to a determined codon.

3. The apparatus of claim 1, further comprising a music signal generator that is configured to receive the melodic sequence and the harmonic sequence and generate a music signal in response to the received melodic and harmonic sequences.

4. The apparatus of claim 1, wherein a root of each determined chord is determined in response to a particular chemical property of the determined amino acid.

5. A method for musically transcribing DNA sequences, comprising:

a. determining a sequence of amino acids from a sequence of nucleotides;
b. determining a sequence of chords in response to the determined amino acid sequence;
c. generating a sequence of tones in response to the nucleotide sequence encoding the amino acid of each determined chord; and
d. generating musical output comprising the determined chords and tones.

6. The method of claim 5, further comprising:
a. determining codons within the received DNA sequence; and
b. synchronizing the harmonic generator in response to the determined codons.

7. The method of claim 5, further comprising generating a music signal in response to the generated melodic and harmonic sequences.

8. The method of claim 7, wherein the music signal is an audio waveform.

9. The method of claim 7, wherein the music signal is a musical command sequence.

10. The method of claim 5, further comprising:
a. classifying the determined amino acid according to a chemical property of the determined amino acid; and
b. determining the chord in response to the classification of the amino acid.

11. The method of claim 5, wherein the melodic sequence is further generated in response to the determined amino acid.

12. A DNA transcriber for generating music, comprising:
a. means for generating a harmonic sequence that is configured to receive a nucleotide sequence, determine an amino acid that is defined by a three-segment nucleotide sequence, and determine a chord in response to the defined amino acid, whereby a harmonic sequence is generated in response to a succession of defined amino acids; and
b. means for generating a melodic sequence that is configured to receive the nucleotide sequence and the chords generated from the determined amino acid sequence, and generate a melodic sequence of tones in response to the received nucleotide sequence within the determined chords.

13. A data carrier comprising the musical output of claim 5.

14. A consumer product comprising the data carrier of claim 13.

15. The consumer product of claim 14, wherein the product is a greeting card.

16. The consumer product of claim 15, wherein the greeting card is an e-card.

17. A method for comparing genetic sequences comprising:
a. generating a first and a second music sample using the method of claim 5;
b. comparing the first and second music samples;
c. generating an audible signal when the first and second music samples differ; and
d. correlating the audible signal with a difference in the compared genetic sequences.

18. An apparatus comprising:
a. a polynucleotide transcriber for receiving a polynucleotide sequence and determining therefrom a sequence of nucleotides and a sequence of amino acids wherein each amino acid is encoded by a triplet of said nucleotides;
b. a harmonic generator for selecting a chord in response to a chemical property of a first determined amino acid of said encoded amino acid sequence;
c. a melodic generator for selecting a first tone of the selected chord in response to a first nucleotide of the triplet encoding the first determined amino acid and for selecting a second tone of the selected chord in response to a second nucleotide of the triplet encoding the first determined amino acid; and
d. an output generator for generating musical commands in response to the selected chord and the selected tones.

19. The apparatus of claim 18, wherein the chord comprises four tones, each tone being associated with a specific nucleotide.

20. The apparatus of claim 18, wherein the melodic generator selects a third tone of the selected chord in response to a third nucleotide of the associated nucleotide triplet.

21. The apparatus of claim 18, wherein the harmonic generator selects a subsequent chord in response to a chemical property of a subsequent amino acid.

22. The apparatus of claim 21, wherein each measure is in ¾ time.

23. The apparatus of claim 18, wherein each triplet corresponds to one measure in the generated musical commands.

* * * * *